United States Patent
Yamada

(10) Patent No.: US 10,060,855 B2
(45) Date of Patent: Aug. 28, 2018

(54) ELECTRIC FIELD ENHANCEMENT ELEMENT AND RAMAN SPECTROMETER

(71) Applicant: Seiko Epson Corporation, Tokyo (JP)

(72) Inventor: Kohei Yamada, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/371,505

(22) Filed: Dec. 7, 2016

(65) Prior Publication Data

US 2017/0160203 A1    Jun. 8, 2017

(30) Foreign Application Priority Data

Dec. 8, 2015 (JP) .................. 2015-239221

(51) Int. Cl.
*G01J 3/28* (2006.01)
*G01N 21/65* (2006.01)
(Continued)

(52) U.S. Cl.
CPC ............. *G01N 21/658* (2013.01); *C09K 9/02* (2013.01); *G01N 33/0037* (2013.01); *C09K 2211/1003* (2013.01)

(58) Field of Classification Search
CPC ... G01J 3/02; G01J 3/44; G01N 21/65; G01N 202/656; G01N 33/0037; G01N 21/658; C09K 9/02

See application file for complete search history.

(56) References Cited

U.S. PATENT DOCUMENTS 7,522,040 B2   4/2009 Passmore et al.
7,547,931 B2   6/2009 Star et al.
(Continued)

FOREIGN PATENT DOCUMENTS

JP    2003-329591 A    11/2003
JP    2007-117782 A    5/2007
(Continued)

OTHER PUBLICATIONS

Graeme McNay et al., "Surface-Enhanced Raman Scattering (SERS) and Surface-Enhanced Resonance Raman Scattering (SERRS): A Review of Applications", Applied Spectroscopy, vol. 65, No. 8, May 27, 2011, pp. 825-837.
(Continued)

*Primary Examiner* — Abdullahi Nur
(74) *Attorney, Agent, or Firm* — Harness, Dickey & Pierce, P.L.C.

(57) ABSTRACT

An electric field enhancement element includes a metal microstructure and a modifying molecule disposed on the surface of the metal microstructure, wherein the modifying molecule is derived from a compound represented by the following formula (1).

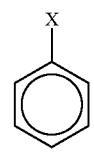

(1)

In the formula (1), X is $-NH_2$, $-SH$, $-Cl$, $-CHO$, $-COOH$, $-SO_3H$, $-CN$, or $-NO_2$.

6 Claims, 8 Drawing Sheets

(51) Int. Cl.
*G01N 33/00* (2006.01)
*C09K 9/02* (2006.01)

(56) References Cited

U.S. PATENT DOCUMENTS

| | | | |
|---|---|---|---|
| 9,204,803 B2 | 12/2015 | Yamada | |
| 9,304,087 B2 | 4/2016 | Yamada | |
| 2012/0327417 A1* | 12/2012 | Amako | G01N 21/658 |
| | | | 356/445 |
| 2017/0079556 A1* | 3/2017 | Hano | A61B 5/082 |

FOREIGN PATENT DOCUMENTS

| | | |
|---|---|---|
| JP | 2009-537219 A | 10/2009 |
| JP | 2013-096939 A | 5/2013 |
| JP | 2014-190909 A | 10/2014 |
| JP | 2015-052463 A | 3/2015 |
| JP | 2016-024070 A | 2/2016 |
| JP | 2017-053638 A | 3/2017 |
| WO | WO-2007-136523 A2 | 11/2007 |

OTHER PUBLICATIONS

N. Bryan Et Al, "Methods to Detect Nitric Oxide and Its Metabolites in Biological Samples", Free Radical Biology & Medicine 43, 2007, pp. 645-657.

T. Nagano Et Al., "Reactions of Nitric Oxide With Amines in the Presence of Dioxygen", Tetrahedron Letters, vol. 36, No. 45, 1995, pp. 8239-8242.

* cited by examiner

| BENZENE RING-BASED MOLECULE | ANILINE (NH₂) | BENZOIC ACID (COOH) | BENZENETHIOL (SH) |
|---|---|---|---|
| E | MEDIUM | MEDIUM | MEDIUM |
| σ | LARGE | MEDIUM | LARGE |
| NO RESPONSE | HIGH | MEDIUM | MEDIUM |

| BENZENE RING-BASED MOLECULE | PHENOL (OH) | CHLOROBENZENE (Cl) | BENZALDEHYDE (CHO) |
|---|---|---|---|
| E | MEDIUM | MEDIUM | MEDIUM |
| σ | SMALL | LARGE | MEDIUM |
| NO RESPONSE | ND | MEDIUM | MEDIUM |

| BENZENE RING-BASED MOLECULE | BENZENE SULFONIC ACID | BENZONITRILE | NITROBENZENE |
|---|---|---|---|
| E | MEDIUM | MEDIUM | MEDIUM |
| σ | MEDIUM | LARGE | LARGE |
| NO RESPONSE | MEDIUM | MEDIUM | MEDIUM |

| ALIPHATIC AMINE | AMMONIA (NH₃) | DIAMINOPROPANE (H₂N-...-NH₂) |
|---|---|---|
| E | HIGH | LOW |
| σ | SMALL | SMALL |
| NO RESPONSE | LOW | LOW |

| THIOL | METHANTHIOL (HS-) | PROPANETHIOL (HS-...) |
|---|---|---|
| E | HIGH | HIGH |
| σ | MEDIUM | MEDIUM |
| NO RESPONSE | ND | ND |

FIG. 8

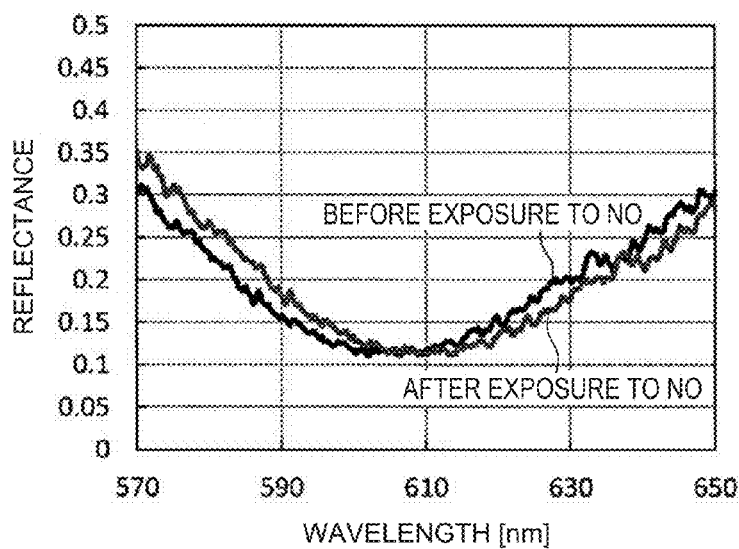
FIG.11
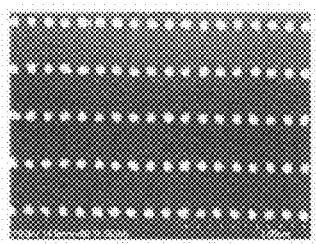 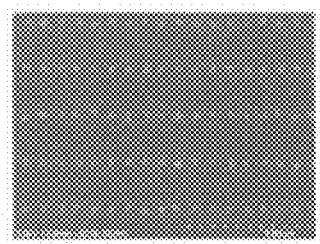 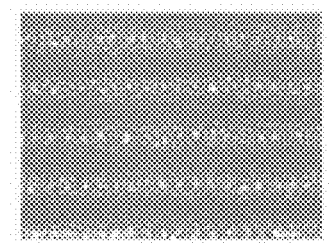
FIG.12A  FIG.12B  FIG.12C
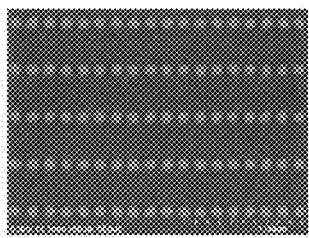 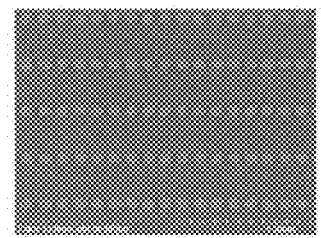 
FIG.13A  FIG.13B  FIG.13C

ELECTRIC FIELD ENHANCEMENT ELEMENT AND RAMAN SPECTROMETER

This application claims the benefit of Japanese Patent Application No. 2015-239221, filed on Dec. 8, 2015. The content of the aforementioned application is hereby incorporated by reference in its entirety.

BACKGROUND

1. Technical Field

The present invention relates to an electric field enhancement element and a Raman spectrometer.

2. Related Art

Recently, as a highly sensitive spectroscopic technique for detecting a sample molecule at a low concentration, an affinity sensor utilizing localized surface plasmon resonance (LSPR) or surface-enhanced Raman scattering (SERS) for qualitative and quantitative detection directly from vibrational spectroscopy has attracted attention. SERS is spectroscopy in which an enhanced electric field is formed on a metal surface with a nanometer-scale rough structures, and Raman scattered light is enhanced by $10^2$ times to $10^4$ times, thereby enabling detection with high sensitivity. A target molecule (target substance) is irradiated with linearly polarized excitation light with a single wavelength such as a laser, and scattered light (Raman scattered light) with a wavelength which is shifted from the wavelength of the excitation light by the molecular vibration energy of the target molecule is spectroscopically detected, whereby a fingerprint spectrum is obtained. Based on the shape of this fingerprint spectrum, the target substance can be identified.

It has been confirmed that there is a correlation between tracheal inflammation due to asthma and the concentration of NO (nitrogen monoxide) contained in the breath, and the concentration of NO in the breath has been recognized as an indicator of asthma. As a sensor chip for detecting such NO, a sensor chip focusing on surface plasmon resonance (SPR) which is a light sensing technique has been proposed. For example, APPLIED SPECTROSCOPY, Volume 65, Number 8, 825-837, 2011 (Non-Patent Document 1) describes that a biological enzyme called "cytochrome P450" is disposed on an LSPR substrate having an Ag microstructure, and NO is allowed to react with the cytochrome P450 enzyme, and the SERS signal of the reactant is obtained.

Here, the distribution of the enhanced electric field induced by surface plasmon resonance exponentially decreases as the distance from the surface of the metal nanoparticle (metal microstructure) of the sensor chip (electric field enhancement element) increases. For example, the result of a test calculation shows that the degree of enhancement at a place more than 3 nm away from the surface of the metal microstructure is decreased to $\frac{1}{200}$ or less of the degree of enhancement on the surface of the metal microstructure. Therefore, it is considered that the sensitivity of sensing using surface plasmon resonance increases as the target molecule is located closer to the surface of the metal microstructure.

The cytochrome P450 described in Non-Patent Document 1 is composed of about 500 amino acid residues and is a high molecular weight protein with heme in the active site. Due to this, even if the cytochrome P450 is disposed on a metal microstructure which induces plasmon resonance, it is difficult to dispose an NO binding portion (binding site) at a distance of 3 nm or less from the surface of the metal microstructure. Therefore, NO may sometimes not be able to be detected with high sensitivity by the technique described in Non-Patent Document 1.

SUMMARY

An advantage of some aspects of the invention is to provide an electric field enhancement element capable of detecting NO (nitrogen monoxide) with high sensitivity. Further, another advantage of some aspects of the invention is to provide a Raman spectrometer including the electric field enhancement element.

An electric field enhancement element according to an aspect of the invention includes a metal microstructure and a modifying molecule disposed on the surface of the metal microstructure, wherein the modifying molecule is derived from a compound represented by the following formula (1).

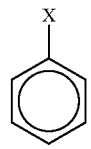

(1)

In the formula (1), X is —$NH_2$, —SH, —Cl, —CHO, —COOH, —$SO_3H$, —CN, or —$NO_2$.

In such an electric field enhancement element, in the modifying molecule, the distance between a metal binding site where the molecule binds to the metal microstructure and an NO binding site where the molecule reacts with an NO molecule can be set to 1 nm or less. Therefore, in such an electric field enhancement element, the modifying molecule can bind to an NO molecule at a place where the degree of enhancement of the electric field enhanced by surface plasmon resonance is high (see "4. Experimental Example" described below). Therefore, in such an electric field enhancement element, NO (NO molecule) can be detected with high sensitivity.

In the electric field enhancement element according to the aspect of the invention, X may be —$NH_2$.

In such an electric field enhancement element, an $NH_2$ group has a strong electron donating property and therefore can serve as an electron donating group which donates an electron to an aromatic ring, and therefore, the reactivity of an NO molecule with an aromatic ring can be further increased.

In the electric field enhancement element according to the aspect of the invention, the material of the metal microstructure may be gold.

In such an electric field enhancement element, the possibility of structural degradation such as migration of the metal microstructure can be reduced, and therefore, long-term stabilization can be achieved.

A Raman spectrometer according to an aspect of the invention includes the electric field enhancement element according to the aspect of the invention, a light source which irradiates the electric field enhancement element with light, and a light detector which detects light emitted from the electric field enhancement element.

In such a Raman spectrometer, the electric field enhancement element according to the invention is included, and therefore, NO can be detected with high sensitivity.

BRIEF DESCRIPTION OF THE DRAWINGS

The invention will be described with reference to the accompanying drawings, wherein like numbers reference like elements.

FIG. 8 is a table showing the results of SERS measurement.

FIG. 11 shows a reflection spectrum.

FIGS. 12A to 12C are photographs showing the results of a degradation test for an Ag element.

FIGS. 13A to 13C are photographs showing the results of a degradation test for an Au element.

DESCRIPTION OF EXEMPLARY EMBODIMENTS

Hereinafter, preferred embodiments of the invention will be described in detail with reference to the drawings. The embodiments described below do not unduly limit the contents of the invention described in the appended claims. Also, all of the configurations described below are not necessarily essential components of the invention.

1. Electric Field Enhancement Element

Figure 1:
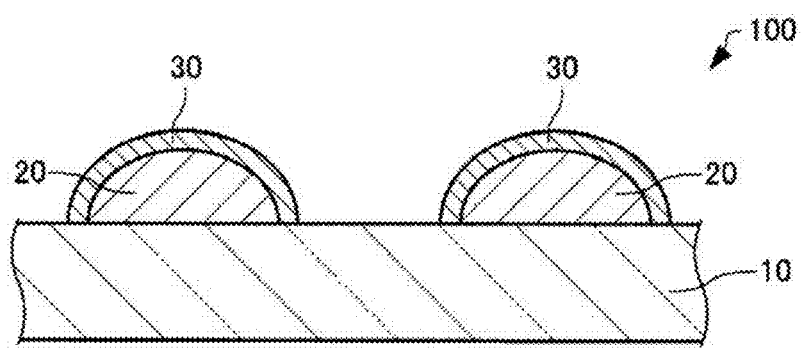
FIG. 1 is a cross-sectional view schematically showing an electric field enhancement element according to an embodiment.
Figure 2:
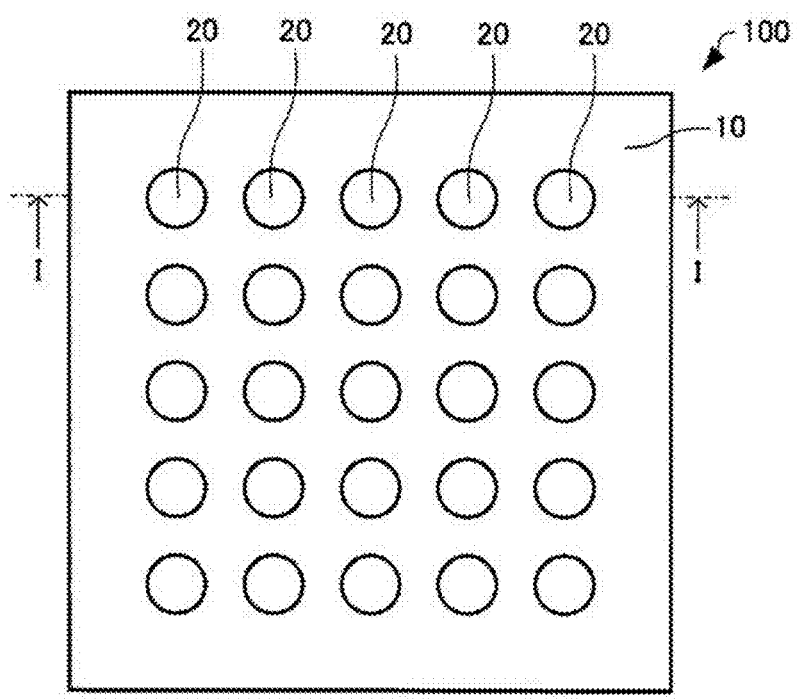
FIG. 2 is a plan view schematically showing an electric field enhancement element according to an embodiment.

First, an electric field enhancement element according to this embodiment will be described with reference to the drawings. FIG. 1 is a cross-sectional view schematically showing an electric field enhancement element 100 according to this embodiment. FIG. 2 is a plan view schematically showing the electric field enhancement element 100 according to this embodiment. FIG. 1 is a cross-sectional view taken along the line I-I in FIG. 2.

As shown in FIGS. 1 and 2, the electric field enhancement element 100 includes a substrate 10, a metal microstructure 20, and a molecular film 30. Incidentally, in FIG. 2, for the sake of convenience, the illustration of the molecular film 30 is omitted.

The substrate 10 is, for example, a glass substrate, a silicon substrate, or a resin substrate. Although not shown in the drawing, between the substrate 10 and the metal microstructure 20, a metal layer provided on the substrate 10 and a dielectric layer provided on the metal layer may be disposed.

The metal microstructure 20 is provided on the substrate 10. The shape of the metal microstructure 20 is not particularly limited, and is, for example, a cylinder, a particle, a prism, a sphere, or a spheroid. In the example shown in FIG. 2, the planar shape of the metal microstructure 20 is a circle. The size (for example, the diameter) of the metal microstructure 20 in plan view is equal to or smaller than the wavelength of the light irradiated on the electric field enhancement element 100. Specifically, the size of the metal microstructure 20 is 10 nm or more and 1 μm or less, preferably 40 nm or more and 700 nm or less. The thickness of the metal microstructure 20 is, for example, 1 nm or more and 500 nm or less, preferably 10 nm or more and 100 nm or less.

For example, a plurality of metal microstructures 20 are provided. The number of metal microstructures 20 is not particularly limited. In the example shown in the drawing, the shapes of the plurality of metal microstructures 20 may be the same as or different from one another. In the example shown in the drawing, the plurality of metal microstructures 20 are periodically provided, but may not be periodically provided. The distance between the adjacent metal microstructures 20 is, for example, 1 nm or more and 500 nm or less.

The material of the metal microstructure 20 is, for example, gold, silver, aluminum, or copper. Gold, silver, aluminum, and copper are metals having a small imaginary part of the dielectric constant in the ultraviolet to visible range, and can increase the electric field enhancement effect. The material of the metal microstructure 20 is preferably gold.

When the metal microstructure 20 is irradiated with light, it generates surface plasmon resonance (SPR). Specifically, the metal microstructure 20 generates localized surface plasmon resonance (LSPR). LSPR is a phenomenon in which when light is incident on a metal structure with a size equal to or smaller than the wavelength of the light, free electrons present in the metal collectively vibrate due to the electric field component of the light, and a localized electric field is induced outside. By this localized electric field, Raman scattered light can be enhanced. In this manner, the enhancement of Raman scattered light by the electric field induced by SPR is called "electric field enhancement effect". The intensity of Raman scattered light (SERS light) enhanced by SPR is proportional to the fourth power of the electric field enhanced by SPR.

The molecular film 30 is provided on the metal microstructure 20. The molecular film 30 includes the modifying molecule according to this embodiment (hereinafter also simply referred to as "modifying molecule"). The modifying molecule is disposed on the surface of the metal microstructure 20. Although not shown in the drawing, the molecular film 30 may be provided also on the substrate 10. The modifying molecule is derived from a compound represented by the following formula (1).

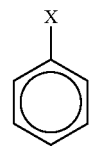

(1)

In the formula (1), X is —NH$_2$, —SH, —Cl, —CHO, —COOH, —SO$_3$H, —CN, or —NO$_2$.

Here, the phrase "the modifying molecule is derived from a compound represented by the formula (1)" refers to that the compound represented by the formula (1) binds to the metal microstructure 20 directly or by detaching a part of a substituent through a bond such as a coordinate bond, a covalent bond, an ionic bond, or a hydrogen bond, whereby a modifying molecule is obtained.

The compound represented by the formula (1) can bind to (can be chemically adsorbed on) the metal microstructure 20 through X. That is, X serves as a metal binding site in the compound represented by the formula (1) where the compound binds to the metal microstructure 20. For example, in FIG. 3, in the case where X is —$NH_2$, a state where the compound represented by the formula (1) (aniline) is bound to the metal microstructure 20 is schematically shown.

Figure 4:
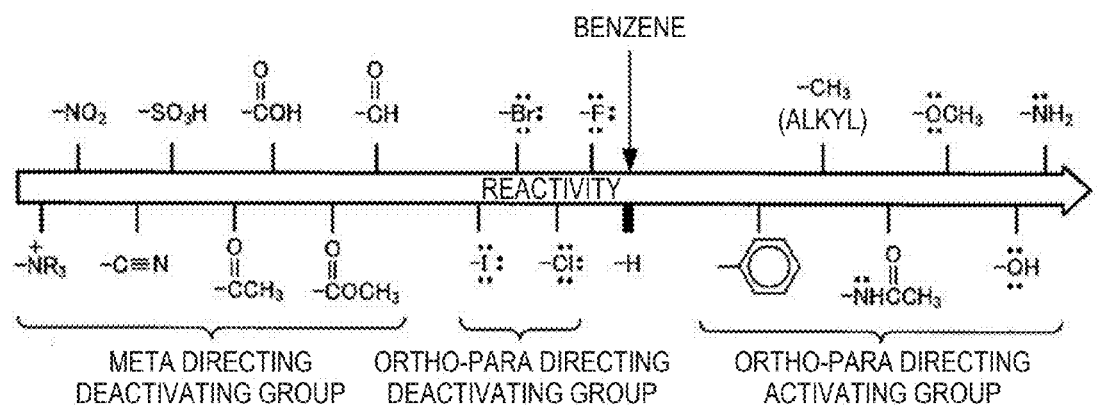
FIG. 4 is a view for explaining the reactivity of a substituent.
Figure 5:
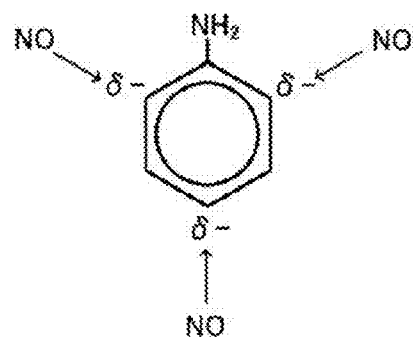
FIG. 5 is a view for explaining a compound (aniline) to serve as a modifying molecule.

In the formula (1), X is preferably —$NH_2$. As shown in FIG. 4, —$NH_2$ has a strong electron donating property and therefore can serve as an electron donating group which donates an electron to an aromatic ring, and therefore, the reactivity of an NO molecule which is a target molecule with an aromatic ring can be increased. Specifically, as shown in FIG. 5, an electron rich site (a part represented by δ- shown in FIG. 5) is locally generated in a benzene ring due to an electron flowing in the benzene ring from —$NH_2$ which is an electron donating group. Then, an NO molecule which has an electron withdrawing property reacts and binds to the electron rich site. That is, the electron rich site serves as an NO binding site where the benzene ring binds to an NO molecule. The reaction rate with an NO molecule is higher than in the case where the substituent (—$NH_2$) is not present (ortho-para directing property).

Figure 3:
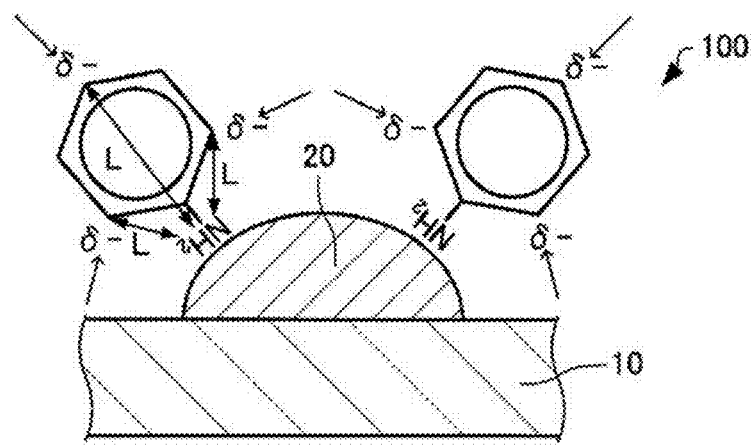
FIG. 3 is a view schematically showing an electric field enhancement element according to an embodiment.

In FIGS. 3 and 5, a site where an NO molecule is likely to bond is indicated by an arrow. Further, FIG. 4 is a view for explaining the reactivity of a substituent, and a group located closer to the right side is a group with higher reactivity, that is, a group having a stronger electron donating property.

More specifically, as represented by the following formula (2), an NO molecule reacts with oxygen in the air and is converted to $N_2O_3$ which is a reactant. Then, as represented by the following formula (3), $N_2O_3$ which has an electron withdrawing property reacts with a benzene ring at an electron rich site, and therefore, a compound derived from aniline is converted to a compound derived from nitroaniline.

$$NO + O_2 \rightarrow N_2O_3 \qquad (2)$$

$$\text{(Compound derived from aniline)} + N_2O_3 \rightarrow \text{(Compound derived from nitroaniline)} \qquad (3)$$

As the electron donating group, other than an $NH_2$ group, a $CH_3$ group, an $NHCOCH_3$ group, a $CH_3O$ group, an OH group, and the like can be exemplified.

In the modifying group, the distance L between the metal binding site and the NO binding site is 1 nm or less. For example, in the example shown in FIG. 3, the compound represented by the formula (1) has three NO binding sites, and the distance L between the metal binding site and each of the three NO binding sites is 1 nm or less. The distance L is preferably 0.5 nm or less, more preferably 0.3 nm or less.

When the electric field enhancement element 100 in a state where an NO molecule is bound to the modifying molecule is irradiated with light (irradiation light), Rayleigh scattered light having the same wavelength as that of the irradiation light and Raman scattered light having a different wavelength from that of the irradiation light are generated. The energy of the Raman scattered light corresponds to the characteristic vibration energy according to the structure in which an NO molecule is bound. Therefore, the concentration of the NO molecule can be found from a Raman shift which is a difference between the wavenumber (the frequency of vibration) of the Raman scattered light and the wavenumber of the irradiation light and the intensity.

Incidentally, an example in which the modifying molecule constitutes the molecular film 30 has been described above, however, the modifying molecule may not be formed into a film. For example, only one modifying molecule may be disposed on the surface of the metal microstructure 20. Further, the molecular film 30 may contain another molecule as long as it contains at least one type of compound represented by the formula (1).

The electric field enhancement element 100 has, for example, the following characteristics.

The electric field enhancement element 100 includes the metal microstructure 20 and the modifying molecule disposed on the surface of the metal microstructure 20, and the modifying molecule is derived from the compound represented by the formula (1). Therefore, in the electric field enhancement element 100, in the modifying molecule, the distance between a metal binding site where the molecule binds to the metal microstructure 20 and an NO binding site where the molecule reacts with an NO molecule can be set to 1 nm or less. Therefore, in the electric field enhancement element 100, the modifying molecule can bind to an NO molecule at a place where the degree of enhancement of the electric field enhanced by surface plasmon resonance is high (see "4. Experimental Example" described below). Therefore, in the electric field enhancement element 100, NO can be detected with high sensitivity.

In the electric field enhancement element 100, in the formula (1), X is —$NH_2$. An $NH_2$ group has a strong electron donating property and therefore can serve as an electron donating group which donates an electron to an aromatic ring. Therefore, in the electric field enhancement element 100, the reactivity of an NO molecule which is a target molecule with an aromatic ring can be further increased.

In the electric field enhancement element 100, the material of the metal microstructure 20 is gold. Therefore, in the electric field enhancement element 100, the possibility of structural degradation such as migration of the metal microstructure 20 can be reduced, and therefore, long-term stabilization can be achieved.

As a method for measuring an NO concentration, there are a chemiluminescence method (chemifluorescence method) in which an NO molecule present in a space is excited by ozone and chemical luminescence generated at that time is measured, and an electrochemical system. The former chemiluminescence method is a very accurate and reliable method, but needs an ozone generator, a vacuum pump, etc., and therefore is expensive and large scale. The latter electrochemical system detects NO by utilizing an electric current generated when NO trapped by an electrode is oxidized and converted to $NO_2^-$, and has an advantage that the configuration of an apparatus can be simplified as compared with the chemiluminescence method, and therefore, the apparatus can be miniaturized. However, the electrochemical system still has problems in terms of selectivity, temperature, humidity, and service life due to electrolyte depletion. In particular, temperature and humidity have a great influence on the sensitivity, and the reproducibility is deteriorated due to variations in the temperature and humidity of breath, and the accuracy is sometimes deteriorated. The electric field enhancement element 100 is inexpensive and has high sensitivity as compared with such a chemiluminescence method and an electrochemical system.

2. Method for Producing Electric Field Enhancement Element

Next, a method for producing the electric field enhancement element 100 according to this embodiment will be described with reference to the drawings.

As shown in FIG. 1, a metal microstructure 20 is formed on a substrate 10. The metal microstructure 20 is formed by, for example, a method in which a thin film is formed by a vacuum vapor deposition method, a sputtering method, or the like, and then patterned, a micro-contact printing method, a nanoimprinting method, or the like.

Subsequently, on the metal microstructure 20, a molecular film 30 is formed. The molecular film 30 is formed by, for example, immersing the substrate 10 having the metal microstructure 20 formed thereon in a solution obtained by diluting a modifying molecule (for example, at a concentration of 1 mM) for a long period of time (for example, 24 hours), and thereafter taking out the substrate 10 from the solution, and then rinsing the substrate 10 with pure water, and blowing off water with an air blow or the like.

By the above steps, the electric field enhancement element 100 can be produced.

3. Raman Spectrometer

Figure 6:
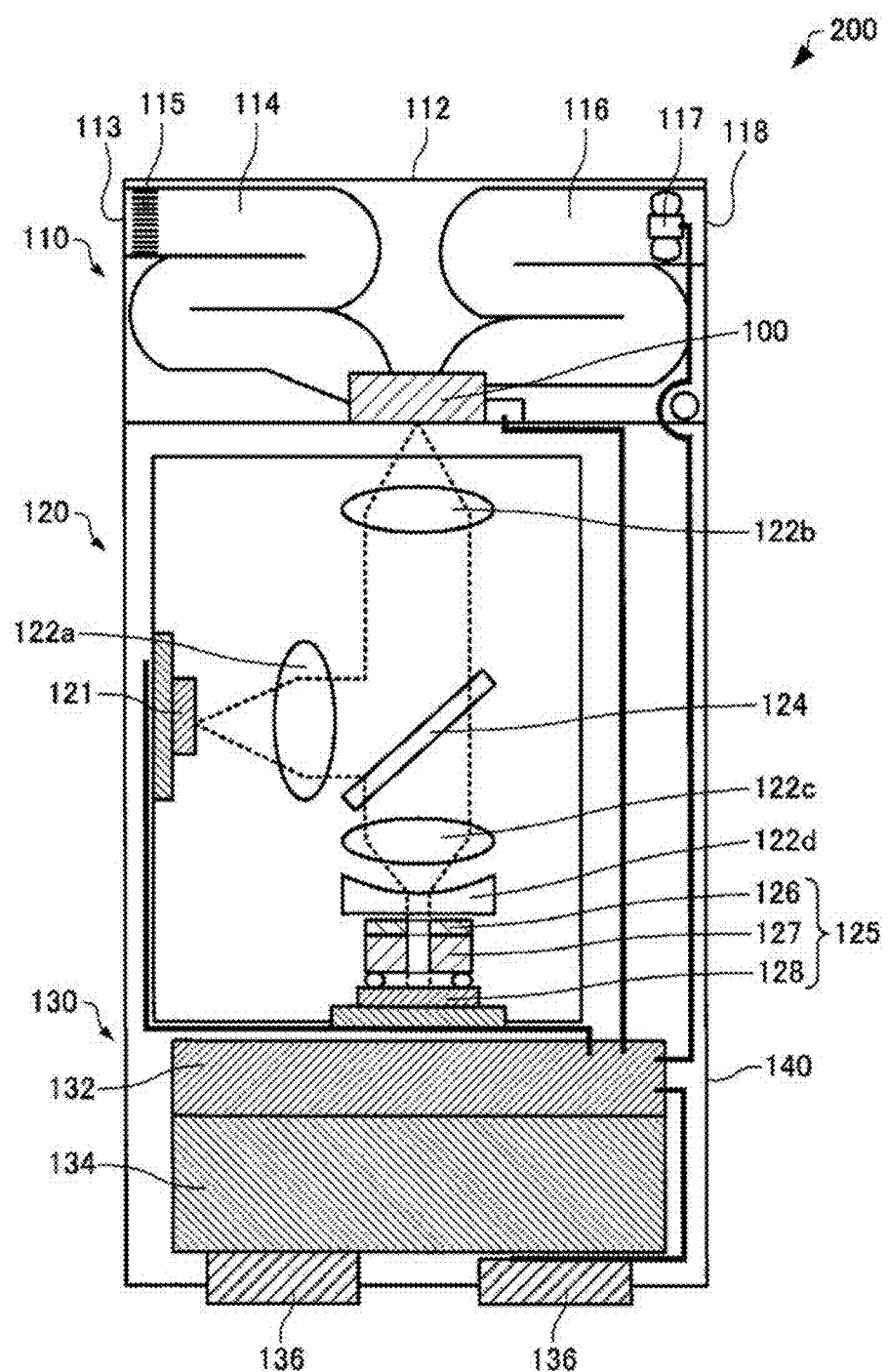
FIG. 6 is a view schematically showing a Raman spectrometer according to an embodiment.

Next, a Raman spectrometer according to this embodiment will be described with reference to the drawings. FIG. 6 is a view schematically showing a Raman spectrometer 200 according to this embodiment.

As shown in FIG. 6, the Raman spectrometer 200 includes a gas sample holding section 110, a detection section 120, a control section 130, and a housing 140 which houses the detection section 120 and the control section 130. The gas sample holding section 110 includes the electric field enhancement element according to the invention. Hereinafter, an example in which the electric field enhancement element 100 is included as the electric field enhancement element according to the invention will be described.

The gas sample holding section 110 includes the electric field enhancement element 100, a cover 112 which covers the electric field enhancement element 100, a suction channel 114, and a discharge channel 116. The detection section 120 includes a light source 121, lenses 122a, 122b, 122c, and 122d, a half mirror 124, and a light detector 125. The control section 130 includes a detection control section 132 which controls the light detector 125 by processing a signal detected in the light detector 125, and an electric power control section 134 which controls an electric power or a voltage for the light source 121 or the like. As shown in FIG. 6, the control section 130 may be electrically connected to a connection section 136 for making the connection to the outside.

In the Raman spectrometer 200, when a suction mechanism 117 provided in the discharge channel 116 is operated, the pressure in the suction channel 114 and the discharge channel 116 becomes a negative pressure, and therefore, a gas sample containing an NO molecule which is a detection target is sucked from a suction port 113. A dust filter 115 is provided for the suction port 113, and therefore, relatively large powder dust, part of water vapor, or the like can be removed. The gas sample passes through the suction channel 114 and the discharge channel 116, and is discharged from a discharge port 118. The gas sample comes into contact with the electric field enhancement element 100 when passing through the channels.

The shape of the suction channel 114 and the discharge channel 116 is a shape such that light from the outside is not incident on the electric field enhancement element 100. According to this, light which becomes a noise other than the Raman scattered light is not incident thereon, and therefore, the S/N ratio of the signal can be improved. The material constituting the channels 114 and 116 is, for example, a material or has a color such that light is hardly reflected.

The shape of the suction channel 114 and the discharge channel 116 is a shape such that the fluid resistance to the gas sample is small. According to this, highly sensitive detection can be performed. For example, by adopting a smooth shape in which corners are eliminated as much as possible as the shape of the channels 114 and 116, the retention of the gas sample in the corners can be eliminated. As the suction mechanism 117, for example, a fan motor or a pump having a static pressure and an air flow according to the channel resistance is used.

In the Raman spectrometer 200, the light source 121 irradiates the electric field enhancement element 100 having an NO molecule bound thereto with light (for example, laser light with a wavelength of 632 nm or excitation light for exciting SPR). As the light source 121, for example, a semiconductor laser or a gas laser is used. The light emitted from the light source 121 is condensed by the lens 122a, and thereafter is incident on the electric field enhancement element 100 through the half mirror 124 and the lens 122b. From the electric field enhancement element 100, SERS light is emitted, and the light reaches the light detector 125 through the lens 122b, the half mirror 124, and the lenses 122c and 122d. That is, the light detector 125 detects light emitted from the electric field enhancement element 100. In the SERS light, Rayleigh scattered light with the same wavelength as the wavelength of the incident light from the light source 121 is contained, and therefore, the Rayleigh scattered light may be removed by a filter 126 of the light detector 125. The light from which the Rayleigh scattered light is removed is received by a light receiving element 128 through a spectroscope 127 of the light detector 125 as Raman scattered light. As the light receiving element 128, for example, a photodiode is used.

The spectroscope 127 of the light detector 125 is formed from, for example, an etalon or the like utilizing Fabry-Perot resonance, and can make a pass wavelength band variable. A Raman spectrum characteristic of the target substance is obtained by the light receiving element 128 of the light detector 125, and for example, by collating the obtained Raman spectrum with the previously stored data, the intensity of the signal of the target substance can be detected.

The Raman spectrometer 200 is not limited to the above-mentioned example as long as it includes the electric field enhancement element 100, the light source 121, and the light detector 125, and is capable of binding an NO molecule to the electric field enhancement element 100 and detecting the Raman scattered light thereof.

The Raman spectrometer 200 includes the electric field enhancement element 100. Therefore, according to the Raman spectrometer 200, an NO molecule can be detected with high sensitivity.

4. Experimental Example

Hereinafter, the invention will be more specifically described by showing an experimental example. Incidentally, the invention is by no means limited to the following experimental example.

4.1. Examination for Detection of NO Molecule by SERS

As described above, an NO molecule promptly reacts with oxygen in the air and is converted to $N_2O_3$ which is a reactant. $N_2O_3$ has strong electrophilicity and therefore has very high reactivity. However, an element in which a metal microstructure composed of Au was formed on a substrate was exposed to NO gas at 20 ppm, and SERS detection (detection of an NO molecule by SERS) was tried, a distinct peak could not be confirmed. On the other hand, there has been a reported case where SERS was detected with respect to NO gas at a concentration on the percent order. Hereafter, an examination for the detection of an NO molecule by SERS was performed.

It was considered that for an element for detecting an NO molecule by SERS, it is important to include a molecular film which satisfies the following three conditions.

(1) The molecular film has a binding site (Au binding site) to a metal microstructure (in this experimental example, Au).

(2) The molecular film has a binding site (NO binding site) to an NO molecule.

(3) The distance between the Au binding site and the NO binding site is 1 nm or less.

With respect to (1), it has been known that an N group, an $NH_2$ group, an SH group, a COOH group, phenol, an $SO_3H$ group, a Cl group, a CHO group, a CN group, an $NO_2$ group, or the like is chemically adsorbed on Au or Ag.

With respect to (2), it has been known that an aliphatic amine or a thiol reacts with NO. Further, the reactant $N_2O_3$ obtained by reacting an NO molecule with oxygen in the air has a strong electron withdrawing property, and therefore, it is considered that also a benzene ring having an electron rich site reacts with an NO molecule.

Figure 7:
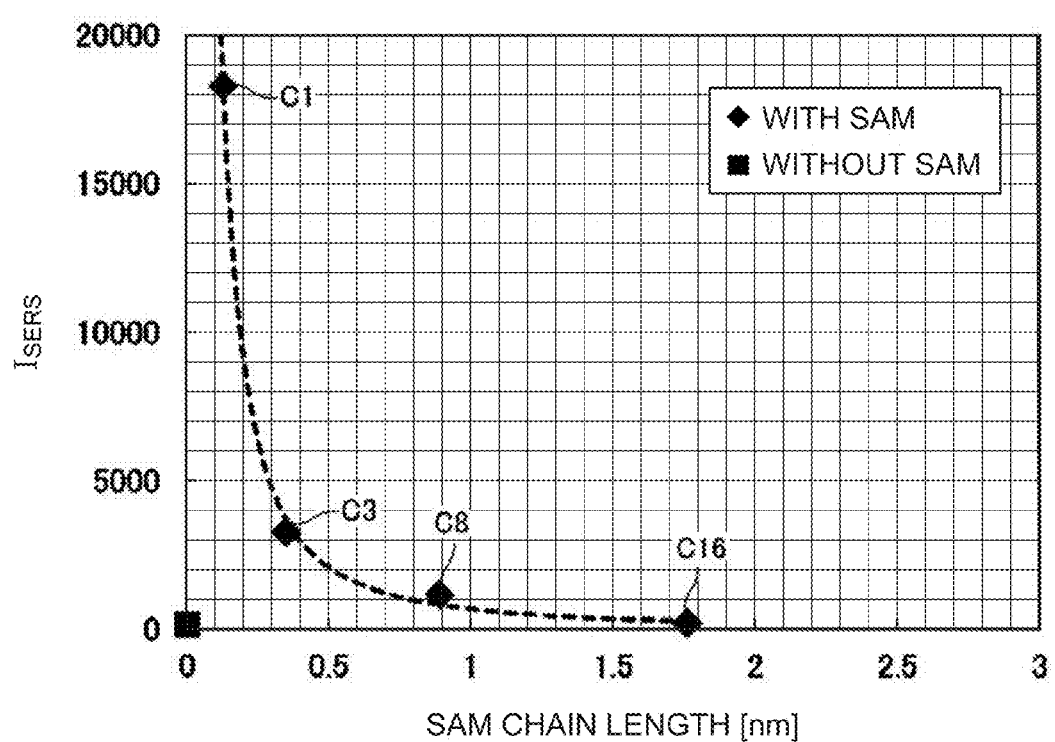
FIG. 7 is a graph showing an SERS intensity.

With respect to (3), as shown in FIG. 7, it is because as the physical properties of surface plasmon resonance, a strong optical electric field is present in a region at a distance of 1 nm or less from a metal surface. When a molecule having an NO binding site is present in this region, Raman scattered light is greatly enhanced, and therefore, NO can be detected with high sensitivity.

Examples of the molecule which satisfies the conditions (1) to (3) include aliphatic amines, thiols, and molecules (benzene ring-based molecules) obtained by substituting H of a benzene ring with any of the following functional groups: an $NH_2$ group, an SH group, a COOH group, an OH group, an $SO_3H$ group, a Cl group, a CHO group, a CN group, and an $NO_2$ group.

FIG. 7 is a graph showing an SERS intensity $I_{SERS}$ for toluene which is a target molecule in an element obtained by providing a molecular film having a molecule derived from an alkanethiol for a metal microstructure composed of Au. The element was exposed to toluene for 60 seconds, and then, the element was irradiated with laser light with a wavelength of 632 nm and an output of 2 mW, and the SERS intensity $I_{SERS}$ was measured. The alkanethiol formed a self-assembled monolayer (SAM) and was chemically adsorbed on Au. More specifically, as the alkanethiol, methanethiol (corresponding to the plot of C1 shown in FIG. 7), propanethiol (corresponding to the plot of C3), octanethiol (corresponding to the plot of C8), and hexadecanethiol (corresponding to the plot of C16) were used, and the measurement was performed. The horizontal axis in FIG. 7 represents the SAM chain length (thickness of the molecular film) and corresponds to the distance between the Au binding site and the NO binding site. The vertical axis in FIG. 7 represents the SERS intensity $I_{SERS}$ (the intensity of Raman scattered light) and is proportional to the fourth power of the electric field E by SERS.

From FIG. 7, it was found that the intensity $I_{SERS}$ increases when the distance L between the Au binding site and the NO binding site is 1 nm or less. It was also found that the intensity $I_{SERS}$ further increases when the distance L is 0.5 nm or less, still further increases when the distance L is 0.3 nm or less. In the case where an SAM was not present, that is, in the case where a molecular film was not provided, toluene could not be detected.

Incidentally, when the Raman scattering cross section is represented by a, the adsorption ratio of the target molecule on the metal microstructure is represented by N, the density of the metal microstructure is represented by D, and the intensity of the electric field enhanced by SERS is represented by E, the SERS intensity $I_{SERS}$ is represented by the following formula (4).

$$I_{SERS} \propto \sigma \times N \times D \times |E|^4 \quad (4)$$

4.2. SERS Measurement

Elements each including a molecular film derived from a molecule listed in the examination in "4.1." described above were formed, and SERS measurement was performed.

After a metal microstructure composed of Au was formed on a substrate, the substrate was immersed in a solution obtained by diluting each molecule (1 mM) for 24 hours. Thereafter, the substrate taken out from the solution was rinsed with pure water, and then water was blown off with an air blow. By the above steps, elements including a molecular film derived from each molecule were formed.

Each element formed as described above was exposed to NO gas at 100 ppb, and SERS measurement was performed. FIG. 8 is a table showing the results of the SERS measurement.

In FIG. 8, the symbol "E" represents the intensity of the electric field enhanced by SERS and is expressed in the following three levels: "high", "medium", and "low". The symbol "σ" represents the Raman scattering cross section and is expressed in the following three levels: "large", "medium", and "small". The "NO response" represents the SERS intensity (the intensity of Raman scattered light) and is expressed in the following four levels: "high", "medium", "low", and "ND". The level "ND" is a case where an NO molecule was not detected. Incidentally, the "E" and "σ" were determined by inference from the results of the "NO response" by simulation or the like.

As shown in FIG. 8, in the case of the aliphatic amines, the NO response was low. This is considered to be because the σ is small. In the case of the thiols, an NO response was not confirmed. This is considered to be because the reaction of HS—R→HS—NO did not occur.

On the other hand, in the case of the benzene ring-based molecules, an NO response was confirmed except phenol. This is considered to be because the SERS intensity of phenol itself when it is adsorbed on a metal such as Au or Ag is low, and therefore, the σ is small.

In the case of the benzene ring-based molecules other than phenol, the NO response was "high" or "medium". This is considered to be because the Raman scattering cross section of the benzene ring is large, and the benzene ring has an electron rich site. Since the benzene ring has an electron rich site, the reactivity of the reactant $N_2O_3$ is considered to be increased because the reactant $N_2O_3$ has an electron withdrawing property. In particular, the element including a molecule derived from aniline has a very high NO response, which was the highest in this experiment. Among the benzene ring-based molecules in which an NO response was confirmed, aniline and benzoic acid are preferred from the viewpoint of safety in handling.

Figure 9:
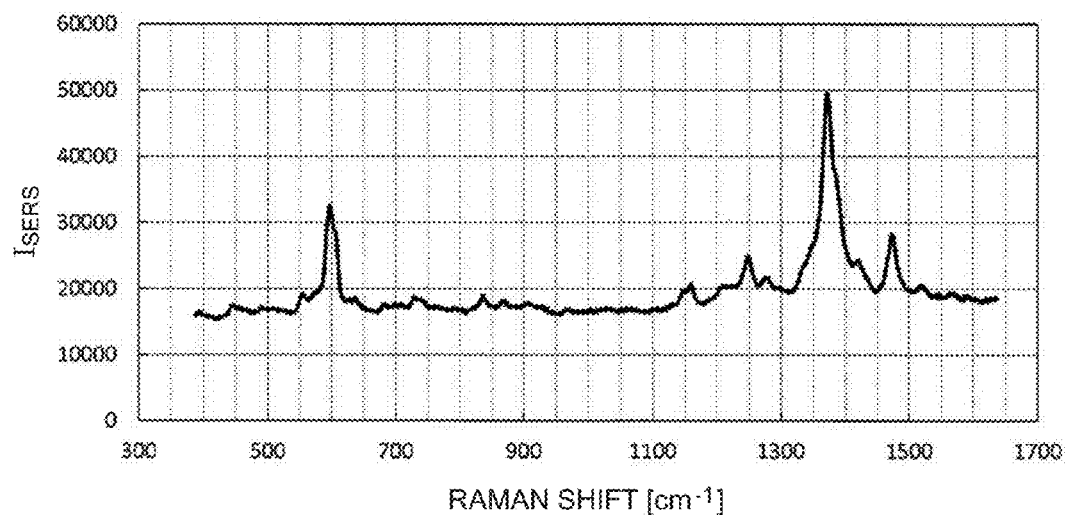
FIG. 9 shows an SERS spectrum.

FIG. 9 shows an SERS spectrum when an element including a molecular film derived from aniline is exposed to NO gas at 100 ppb. As the irradiation light, laser light with a wavelength of 632 nm and an output of 0.5 mW was used. As the $I_{SERS}$ represented by the horizontal axis in FIG. 9, a difference obtained by subtracting a spectrum before the element was exposed to NO gas from a spectrum after the element was exposed to NO gas is shown.

As shown in FIG. 9, strong peaks were confirmed at 600 cm$^{-1}$ and 1374 cm$^{-1}$. This coincides with the frequency band derived from an NO$_2$ group, and therefore, it is considered that aniline reacted with an NO molecule and was converted to nitroaniline.

4.3. Method for Detecting NO Using Peak Shift

An NO molecule could be detected using a peak shift without using SERS, which will be specifically described below.

Figure 10:
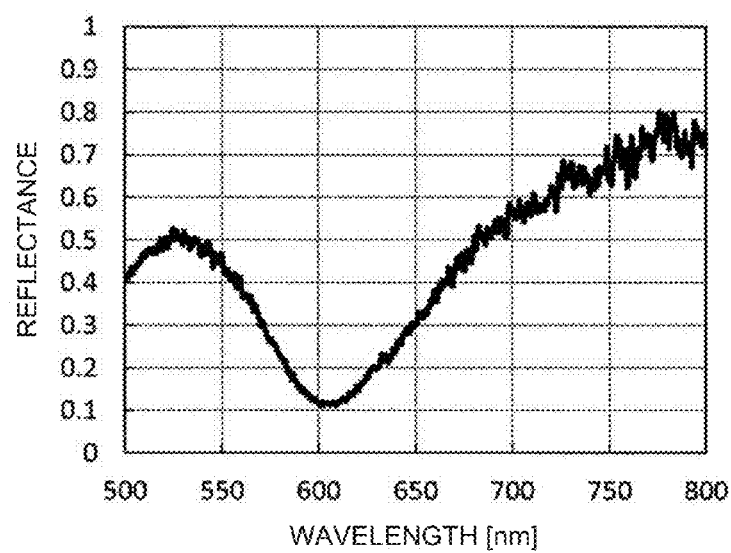
FIG. 10 shows a reflection spectrum.

FIG. 10 shows a reflection spectrum of an element including a molecular film derived from aniline (the same element as the element used for the measurement in FIG. 9). As shown in FIG. 10, a peak derived from plasmon resonance was confirmed at around 605 nm.

After the above-mentioned element was exposed to NO gas at 20 ppm for a sufficient time, a reflection spectrum was obtained (see FIG. 11). The peak derived from plasmon resonance shifted by about 5 nm from 605 nm to 610 nm. The NO concentration may be determined from the amount of peak shift based on a previously prepared calibration curve, however, the peak derived from plasmon resonance is broad, and therefore, it is sometimes difficult to read the wavelength of the peak with high accuracy. Therefore, by reading the amount of change in the reflectance at a wavelength position shifted from the peak, the shift amount can be read with high accuracy and high sensitivity. In general, the reflectance resolution is higher than wavelength resolution.

For example, in FIG. 11, at a wavelength of 590 nm, the reflectance shifts from 0.1545 to 0.1718. By previously preparing a calibration curve for the amount of change in the reflectance at an arbitrary wavelength with respect to the NO concentration for exposure, the NO concentration can be determined from the amount of change in the reflectance.

In this method, the measurement can be performed using only a single color LED (Light Emitting Diode) light source and a photodiode (PD), and therefore, this method costs less than a Raman spectroscopy using a laser light source, a spectrometer, or the like, and the apparatus can be miniaturized.

4.4. Degradation Test for Metal Microstructure

A degradation test was performed for an element in which a metal microstructure composed of Ag was formed on a substrate (Ag element) and an element in which a metal microstructure composed of Au was formed on a substrate (Au element). Specifically, the Ag element and the Au element were stored in an atmosphere at a temperature of 23° C. and a humidity of 54%, and a structural change in the metal microstructure was confirmed using a metallographic microscope.

FIGS. 12A to 12C are photographs showing the results of the degradation test for the Ag element. FIGS. 13A to 13C are photographs showing the results of the degradation test for the Au element. In FIGS. 12A to 13C, FIGS. 12A and 13A are photographs immediately after forming the metal microstructure, FIGS. 12B and 13B are photographs after a lapse of 7 days from the formation, and FIGS. 12C and 13C are photographs after a lapse of 14 days from the formation.

As shown in FIGS. 12A to 12C, in the Ag element, the metal microstructure was degraded as days went by. On the other hand, as shown in FIGS. 13A to 13C, in the Au element, a structural change (degradation) such as migration was not confirmed. Although not shown in the drawing, in a dehumidified environment, a structural change was not confirmed also in the Ag element. Therefore, it could be figured out that the degradation of the Ag element as shown in FIGS. 12A to 12C was caused by a reaction between Ag and water. By this test, it was found that long-term stabilization of the metal microstructure composed of Au can be achieved.

The electric field enhancement element according to the invention may also be applied to surface-enhanced infrared absorption spectroscopy (SEIRAS) using SPR. Further, an example in which an NO molecule is used as a target molecule has been described above, however, the electric field enhancement element according to the invention can be applied to a target molecule having an electron withdrawing property other than an NO molecule.

The invention includes substantially the same configurations (for example, configurations having the same function, method, and result, or configurations having the same object and effect) as the configuration described in the embodiment. Further, the invention includes configurations in which a nonessential part of the configuration described in the embodiment is replaced. In addition, the invention includes configurations having the same operational effect as that of the configuration described in the embodiment, or configurations capable of achieving the same object. Moreover, the invention includes configurations in which a known art is added to the configuration described in the embodiment.

What is claimed is:
1. An electric field enhancement element, comprising:
a metal microstructure; and
a modifying molecule disposed on the surface of the metal microstructure, wherein
the modifying molecule is derived from a compound represented by the following formula (1):

(1)

wherein X is —NH$_2$, —SH, —Cl, —CHO, —COOH, —SO$_3$H, —CN, or —NO$_2$.

2. The electric field enhancement element according to claim 1, wherein X is —NH$_2$.

3. The electric field enhancement element according to claim 1, wherein the material of the metal microstructure is gold.

4. A Raman spectrometer, comprising:
the electric field enhancement element according to claim 1;
a light source which irradiates the electric field enhancement element with light; and
a light detector which detects light emitted from the electric field enhancement element.

5. A Raman spectrometer, comprising:
the electric field enhancement element according to claim 2;
a light source which irradiates the electric field enhancement element with light; and
a light detector which detects light emitted from the electric field enhancement element.

6. A Raman spectrometer, comprising:
the electric field enhancement element according to claim 3;
a light source which irradiates the electric field enhancement element with light; and
a light detector which detects light emitted from the electric field enhancement element.

* * * * *